United States Patent
Dwork

[19]

[11] Patent Number: 6,113,582
[45] Date of Patent: Sep. 5, 2000

[54] MALE URINARY INCONTINENCE DEVICE

[76] Inventor: Paul Dwork, 1127 Garrido Dr., Camarillo, Calif. 93010

[21] Appl. No.: 09/262,523

[22] Filed: Mar. 4, 1999

[51] Int. Cl.[7] ........................................................ A61F 5/44
[52] U.S. Cl. ........................... 604/349; 604/351; 604/353
[58] Field of Search ..................... 604/349, 351, 604/353, 347, 346, 350, 317, 352, 354

[56] References Cited

U.S. PATENT DOCUMENTS

| | | |
|---|---|---|
| 719,811 | 2/1903 | Kent . |
| 1,105,488 | 7/1914 | Clare . |
| 2,310,505 | 2/1943 | Blackburn et al. . |
| 2,445,694 | 7/1948 | Predmore . |
| 3,526,227 | 9/1970 | Appelbaum . |
| 4,553,968 | 11/1985 | Komis . |
| 4,601,716 | 7/1986 | Smith . |
| 4,713,067 | 12/1987 | Rothenberg et al. . |
| 4,790,834 | 12/1988 | Austin . |
| 4,997,427 | 3/1991 | Bowen . |
| 5,009,649 | 4/1991 | Goulter et al. . |
| 5,032,118 | 7/1991 | Mason . |
| 5,065,459 | 11/1991 | Tjahaja et al. . |
| 5,147,341 | 9/1992 | Starke et al. . |
| 5,195,997 | 3/1993 | Carns . |
| 5,267,989 | 12/1993 | Moyet-Ortiz . |
| 5,346,483 | 9/1994 | Thaxton, Sr. . |
| 5,366,449 | 11/1994 | Gilberg . |
| 5,423,785 | 6/1995 | Hart ......................................... 604/353 |
| 5,478,334 | 12/1995 | Bernstein ................................. 604/353 |
| 5,618,277 | 4/1997 | Goulter ..................................... 604/349 |
| 5,643,235 | 7/1997 | Figuerido ................................. 604/352 |
| 5,695,485 | 12/1997 | Duperret et al. . |
| 5,797,890 | 8/1998 | Goulter et al. . |

*Primary Examiner*—Sharon Kennedy
*Assistant Examiner*—Eric Kline
*Attorney, Agent, or Firm*—Shanks & Herbert

[57] ABSTRACT

A fluid tight wrap is provided around a penis of a user utilizing a substantially fluid impermeable sheath formed of sheet material. The sheath has a proximal end and a distal end, an inner surface and an outer surface, where the inner surface contacts the skin of the penis in use. The sheath has a first side and a second side, and sheath member is sized to circumferentially envelop a penis of a user such that the inner surface of the second side overlaps the attachment portion and the attachment portion securing the second side to the first side such that the first and second sides overlyingly coextend substantially longitudinally down the penile shaft from the proximal end of the sheath to the distal end of the sheath.

20 Claims, 8 Drawing Sheets

MALE URINARY INCONTINENCE DEVICE

BACKGROUND OF THE INVENTION

1. Field of the Invention

The present invention relates to urinary incontinence in general, and more specifically to a male urinary incontinence device using a wrap for enveloping the penis.

2. Background

Urinary Incontinence (UI) is a very common problem in the United States estimated to afflict more than 13 million people. Of those afflicted, about one third are men. The total annual cost of providing care for persons with UI is estimated to be $16 billion. The market for adult absorbent devices or diapers alone in 1994 was $1.5 billion projected to be growing about 25% per year. As the demographics in the United States shift to a more aged population, and as society in general becomes increasingly mobile, the increasing number of persons suffering from, and demanding solutions for UI will simultaneously increase.

UI can affect persons of all ages, and may be the result of physical disability or a psychological condition. There are several different types of incontinence, which are outlined below.

Acute (or Transient) Incontinence is caused by generally treatable medical problems. Medical conditions such as dehydration, delirium, urinary retention, fecal impaction/constipation, urinary tract infection and atrophic vaginitis can cause an onset of UI. In addition to medical problems, certain medications can cause or contribute to an incontinence problem, such as anticholinergic agents, antihistamines, antidepressants (tca), phenothiazines, disopyramides, opiates, antispasmodics, parkinson drugs, alpha-adrenergic agents (high blood pressure drugs), sympathomimetics (decongestants), and sympatholytics (e.g., prazosin, terazosin, and doxazosin).

Chronic UI is by definition an ongoing and therefore more difficult to treat affliction. Chronic UI is conventionally classified into four groups: Stress, Urge, Overflow, and Functional incontinence. They may occur alone or in combination, the latter being more common as the patient ages.

Stress incontinence is the involuntary leakage of small amounts of urine in response to increased pressure in the abdomen. Incontinence will usually occur during physical events, such as sneezing, coughing, laughing, bending, lifting, etc. Although stress incontinence is predominantly a female affliction, men can also suffer from stress incontinence. Stress incontinence in men usually results from a weakened function of the urethral sphincter that surrounds the prostate, sometimes as a result of prostate surgery.

Urge incontinence is the most common pattern of UI in the older person, and is characterized by insufficient control during the time between the urge to void and the start of urination. One cause of urge UI is detrusor hyperreflexia or instability which is associated with disorders of the lower urinary tract or neurologic system. Urge incontinence can also be the result of urologic carcinoma, diverticula, or other physical abnormalities.

Overflow incontinence accounts for 10–15% of urinary incontinence. Overflow UI is usually the result of an obstruction (e.g., enlarged prostate, urethral stricture) of the bladder outlet or an atonic bladder as the result of neurologic injury (e.g., spinal chord trauma, stroke), diabetic neuropathic bladder, or drug-induced atonia. The obstruction leads to bladder overfilling, resulting in a compulsive detrusor contraction. In this form of UI chronic "dribbling" is common. Drug induced atonia can be caused by anticholinergics, narcotics, anti-depressants, and smooth muscle relaxants.

Functional incontinence accounts for 25% of all incontinence and results when a person is confined and sedentary, such as in a nursing home or during a long period of convalescence. Functional incontinence is sometimes diagnosed as a result of the victim simply being unable to communicate his or her needs, or through other sensory impairments that make the victim unaware of his or her need to void. This condition can further result from decreased mental unction, decreased functional status, and/or a simple unwillingness to physically go to the toilet.

Incontinence is also frequent among persons rehabilitating from stroke, head injury, multiple sclerosis, amputations, and spinal cord injury.

Enuresis, or bedwetting, is a form of incontinence that is very common among preschool children, and often persists into adulthood. Enuresis can cause degraded self-esteem, and may lead to social withdrawal at an early age. The bedwetter may be reluctant to attend sleep over social events with his or her friends. Most often, the reason a child or adult will have the problem of nocturnal enuresis is because they simply cannot wake up. Nocturnal enuresis afflicts approximately 15–20% of school age children between the ages of 4 and 16. Treatment of enuresis typically requires training the person to recognize the need to urinate during sleep, or to train the person to sleep correctly. Moisture sensing alarms have been successfully employed, but if soiled bedding are to be avoided, require the use of diapers or other absorbent padding.

Some symptoms of UI that interfere with quality of life include leaking urine when coughing, sneezing, laughing or exercising; waking up multiple times at night to go to the bathroom; the need to know the locations of bathrooms when on travel or shopping; and the leaking of urine during sex. UI can obviously lead to discomfort and embarrassment, and eventually to social withdrawal and isolation. Excursions outside the home, social interaction, and sexual activity may be restricted or avoided entirely in the presence of incontinence. In older persons, UI is the predominant reason aging parents are put into nursing homes, because of the burden UI places on caregivers.

Means for aiding incontinence in the prior art include catheterization, absorbent products, and for males, devices attached to the exterior surface of the penis to collect urine discharge. For children prone to bedwetting, various approaches are also available, for example wet-bed alarm systems, which are readily available and easy to use, and Desmopressin acetate (synthetic ADH), a nasal spray.

Catheterization is an unattractive option to many persons suffering from UI because of the risks associated with an indwelling catheter. The catheter may be retained permanently in the bladder draining freely into a collection bag. In the permanent arrangement, the catheter is held in the bladder by a balloon, usually inflated with sterile water. The catheter may also be inserted intermittently on an as-needed basis. This approach is very inconvenient and many patients are psychologically averse to self-catheterization, or physically unable to perform the manipulations required.

Long term use of indwelling catheters presents further problems. Within 2 to 4 weeks after permanent catheterization, the urine of virtually every patient is contaminated by bacteria. Catheter-associated bacteriuria represents the most common infection acquired in acute care and long-term care facilities. Complications ranging from bladder spasms and catheter leakage to death caused by septicemia are also well known limitations. Bacterial entry into the bladder occurs either from extraluminal migration along the outside of the catheter, contamination on insertion of the catheter, or contamination of the drainage bag, leading to bacterial growth and subsequent migration into the bladder.

Accordingly, catheterization is overall the least preferred type of bladder management.

Absorbent devices, such as diapers, are the most popular remedy, accounting for billions of dollars in annual sales in the US. They are easily obtained, and can address acute UI symptoms quickly. While affording somewhat effective control of urine and providing mobility to the patient, the absorbent method suffers from very serious drawbacks. /

First, absorbent devices do not remove urine to a point distal from the genital region, they simply absorb and disperse the urine in order to manage it. This, of course, leads to urine soaked absorbent being in contact with the skin, which causes irritation and discomfort. Most advances in the art deal with providing different absorbent layers to attempt to direct the urine to migrate to a region away from the skin, with limited success.

Absorbent devices also disadvantageously rely on providing a large area of absorbent, usually in the form of pants or diapers. Not only is such an arrangement uncomfortable, it requires involved procedures for applying and removing the device. Further, the diaper pants must be removed in order to defecate, apply medications to the groin area, etc. Once removed, whether soiled or not, the disposable-type diaper usually must be disposed of, creating the need to always carry a supply of such absorbent devices.

A major problem with absorbent devices is that of odor. Urine has a distinctive and recognizable odor which is embarrassing to most people. Various approaches have been taken in order to control urine odor with absorbent devices, with limited success.

In men, an alternative to the indwelling catheter or absorbent device is an external collecting device which is fitted over the male genitalia, like a condom, and connected via a catheter to a drainage bag held onto the body by leg straps, or by special devices like the one leg pant marketed by NETTI®. Several such "external catheter" devices are described in the prior art.

U.S. Pat. Nos. 5,797,890 and 5,009,649 describe male UI condom catheters. In these type devices, a latex or similar material condom is unrolled onto the penis, sealingly engaging the same. An extended fluid collection region extending from the distal end of the device provides a reservoir for collected urine. The condom is additionally held to the penis by means of a band, for example using VELCRO®. The '890 patent additionally provides a ring mounted on a simple garment support that allows the rolled, proximal end of the condom to be unrolled about the ring, allowing additional support of the device, but requiring that the frequently flaccid penis be inserted under axial load into the condom.

These devices are disadvantaged by the complexity of their application, and the requirement that the condoms be properly sized for the device to function properly. The application of the condom member requires some degree of dexterity to position and unroll the condom onto the penis, which is frequently flaccid. The flaccid state of the penis renders the seal created by the condom variably effective, and frequently inadequate. Further, in the case of a patient deprived of the full use of his motor skills, for example a stroke patient or MS sufferer, the task may be impossible. Frequently, the issue of condom sizing creates difficulties, when the purchaser is other than the user, or when the user is less than sure about his relative girth.

A further severe disadvantage with this type of device is that should the evacuation tube at the distal end of the condom become kinked or blocked, urine pressure will build in the condom until urine is forcefully ejected along the side of the condom, the condom breaks, or the entire apparatus slips from the penis. The spread of urine up the shaft of the penis lowers the friction between the condom and the penile shaft, increasing the chances of the penis slipping from the condom. Such events can be extremely messy, causing the forceful discharge of a substantial amount of urine into the pants of the wearer.

Other devices comprise a loose-fitting sleeve for the penis, such as the McGuire style mail urinal. The urinal, which is in effect a bag into which the penis extends, is used in conjunction with a valved tube leading to a leg bag. In theory, the urinal drains into the leg bag. These devices create serious problems with poor sealing and spillage of urine around the penis, and even present the problem of a flaccid and withdrawn penis pulling out of the sleeve altogether. Because the device relies on gravity to feed urine from the urinal to the leg bag, use during sitting can be messy or uncomfortable.

Improvements to the prior art are continually being sought.

SUMMARY OF THE INVENTION

The present invention provides a male urinary incontinence device which overcomes the problems of the prior art. The invention permits facile, one-handed mounting onto any sized male member, even if flaccid and withdrawn, and provides for positive sealing and isolation of the skin and the outside environment from urine.

According to the invention, a fluid tight wrap is provided around a penis of a user utilizing a substantially fluid impermeable sheath formed of sheet material. The sheath has a proximal end and a distal end, an inner surface and an outer surface, where the inner surface contacts the skin of the penis in use. The sheath has a first side and a second side, and sheath member is sized to circumferentially envelop a penis of a user such that the inner surface of the second side overlaps the attachment portion and the attachment portion securing the second side to the first side such that the first and second sides overlyingly coextend substantially longitudinally down the penile shaft from the proximal end of the sheath to the distal end of the sheath.

Features of the invention include a relatively flat bearing ring for surrounding the penis at the base of the shaft for advantageously posturing the penis for application of a penis sheath. The ring advantageously provides a rigid, stable, hair-free surface for mounting the remaining parts of the apparatus.

A further feature of the invention includes a sheath which is wrapped about the penis, distributing sealing pressure evenly over the surface of the organ.

A still further feature of the invention is a separate urine chamber, which sealingly attaches to the exterior of the sheath and to a bag or the like.

A further feature of the invention includes a closed system for handling urine from a patient suffering from urinary incontinence, thus eliminating unpleasant odor.

An advantage of the present invention is a one size fits all approach that allows for simpler and less embarrassing purchasing decisions.

A further feature of the present invention is a male UI device which is reusable and economical to maintain.

Yet another advantage of the instant invention is that it is usable with bedwetting alarms, allowing corrective training of children without soiled bedding.

BRIEF DESCRIPTION OF THE DRAWINGS

The foregoing and other features and advantages of the present invention will be more fully understood from the following detailed description of an illustrative embodiment, taken in conjunction with the accompanying drawing in which.

DETAILED DESCRIPTION OF AN ILLUSTRATIVE EMBODIMENT

The present invention will be described herein with reference to an illustrative embodiment of a male urinary incontinence device.

Figure 1:
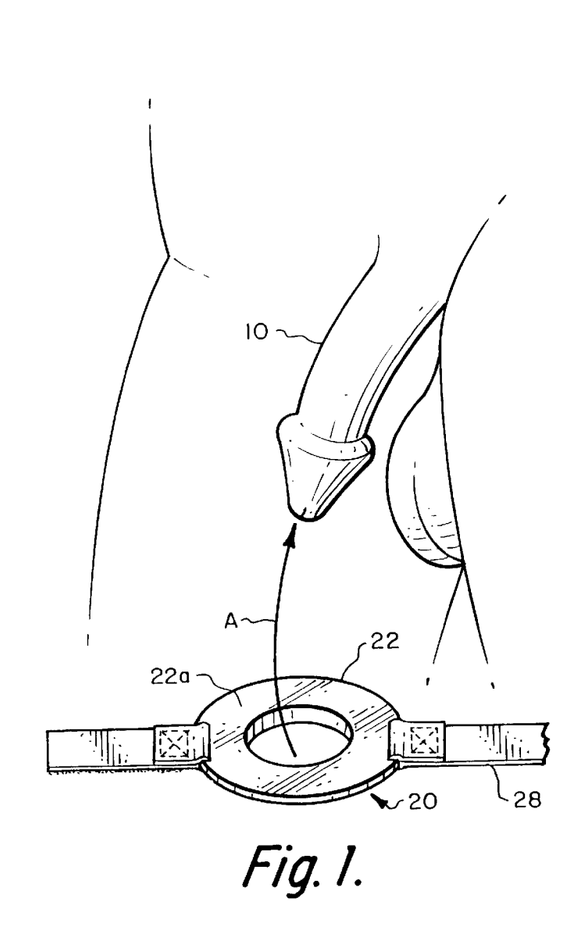
FIG. 1 is a perspective view of the retention ring positioned for mounting on a patient.
Figure 2:
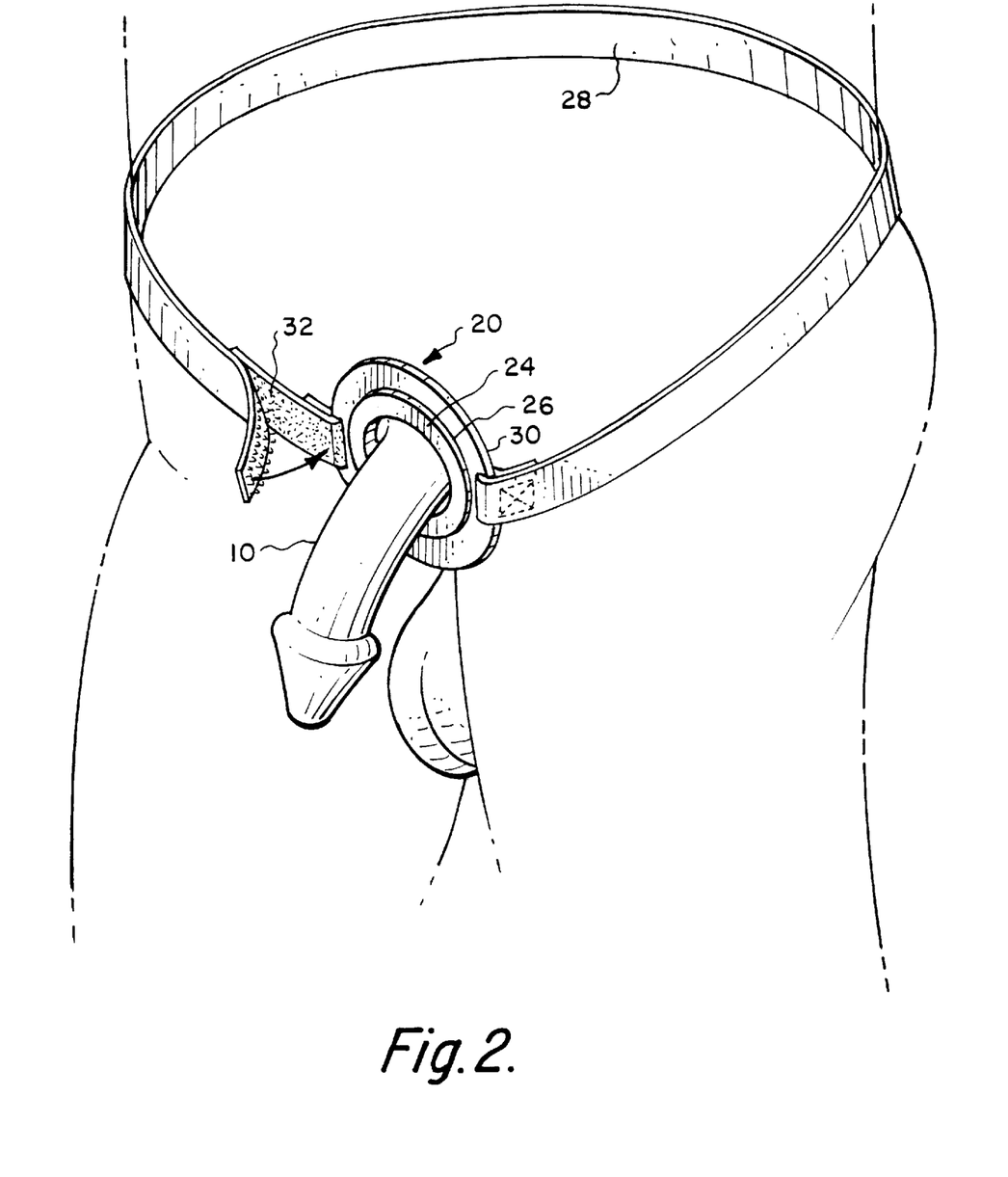
FIG. 2 is a perspective view of the retention ring mounted on a patient.

Referring to FIG. 1, the male patient is depicted having a penis 10. A retention assembly 20 is mounted to the patient as depicted by the arrow A and as further shown in the following Figures. The retention assembly 20 has a retention body 22, which is a generally flat or contoured member having a hole which accommodates the insertion of the penis therethrough. A flat side 22a of the retention body 22 is, in use, pressed against the body of the patient. A band 28 holds the retention body 22 to the patient in known fashion. In use, the penis is inserted in the hole of the retention body 22, and the band adjusted such that the flat side 22a of the retention body presses against the patient to the extent necessary to urge the penis 10 through the hole, as depicted in FIG. 2. In patients having a withdrawn penis due to obesity or other anatomic features, the retention body allows the penis to be urged through the hole to the extent necessary to attach the device, as will be discussed hereinbelow.

As further shown in FIG. 2, the band 28 passes through securing structures, such as slots 30, on the retention body 22. The band 28 is attached by a band attachment structure 32 which can be hook and loop fastener, adhesive, clasps, hooks, elastic, piton and hole arrangements, clips, clamps, strap locks, and the like. The band can be of any suitable material, either woven or otherwise, elastic or inelastic, based on the preferences of the user. The band can also be in the form of a garment, such as briefs, pants or the like.

Also depicted is an attachment flange 24, underlying which is a groove 26 which cooperates with retaining structure of a sheath wrap as discussed in greater detail hereinbelow.

The retention body 22 is depicted as being a hollow disk, but other shapes are of course possible. The outer peripheral shape of the retention body can be any shape which provides comfort, sufficient strength, and adequate attachment points for the band 28. The band 28, while illustrated as a waist band, can also attach to other an atomical features, for example the legs depending on the patient. The hole in the retention body should be wider than the penis, and provide adequate clearance in the case of an erection. The preferred material is high-impact molded plastic for strength, cost and ease of cleaning, but other materials such as metal, composites, and the like are also possible.

Figure 3:
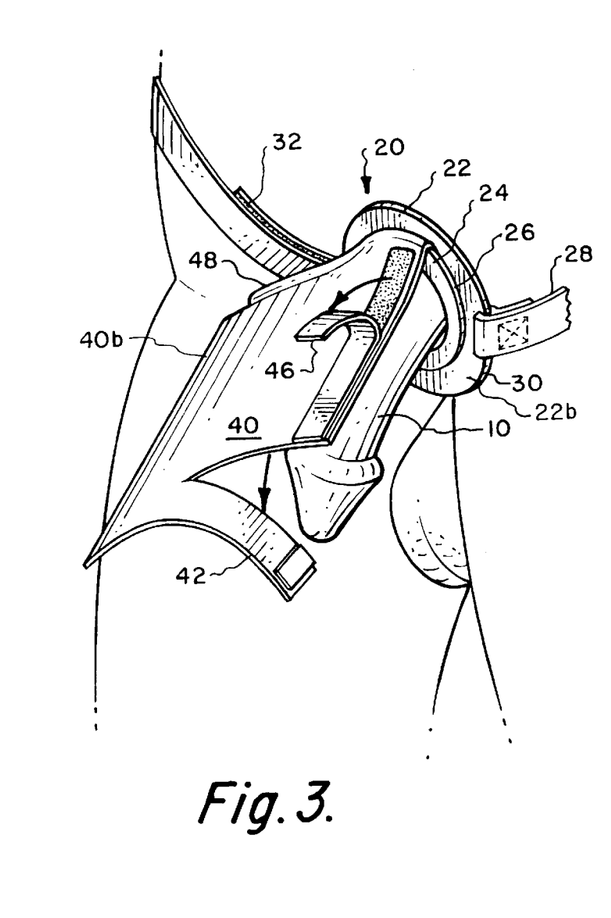
FIG. 3 is a perspective view of a wraparound sheath according to the invention being applied to the retention ring of FIGS. 1 and 2 and the patient.

Referring now to FIG. 3, the application of the sheath wrap 40 is depicted. The sheath wrap 40 is applied circumferentially about the phallus 10 to envelop the same. The sheath wrap is applied in contrast to a condom, which is unrolled up the shaft of the penis 10. The sheath wrap 40, being formed of a flexible sheet of material such as latex, urethane, or the like, can be easily trimmed to size, as depicted by extra material 42 being removed. Of course, indicia (not shown) can be positioned on the sheath wrap 40 to aid in trimming. Extending longitudinally down the sheath wrap is an attachment portion 44, which may be an adhesive strip provided with a removable backing 46. Of course other attachment means are usable, such as adhesives, hook and loop fasteners, and the like, or the sheath wrap can be treated over a portion of the surface to form a secure bond to a mating surface. Extending laterally across the proximal edge of the sheath wrap 40 is a sheath retention portion 48, which in the illustrative embodiment is in the form of a thickened bead portion stably receivable in the groove 26 of the retention body 22. In applying the sheath wrap 40 to the penis, the retention portion 48 may be pushed into the groove 26 of the retention body in a circular motion by the thumb, following the fingers which wrap the sheath around the penis. The penis is advantageously urged forth from the hole in the retention body, providing firm graspability of the penis shaft. After the sheath wrap 40 has surrounded the penis, the attachment portion 44 is activated and the sheath secured. In the illustrative embodiment, activation of the attachment portion 44 would comprise removing the adhesive backing 46 and pressing the opposite longitudinal region 40b to the exposed adhesive 44. The penis is thus enveloped in the sheath wrap.

The retention portion 48 of the sheath wrap 40 can also be an adhesive ring, a velcro loop attachment, or other means known in the art.

It should be noted that although the overlap of the sheath portions extends between the distal and proximal ends in a longitudinal direction, the overlap can be of any convenient shape, and may even comprize horizontal tabs which are individually secured. For example, it may be convenient to have the longitudinal region 40b formed in a staggered or other irregular shape to aid in gripping during removal.

Figure 4:
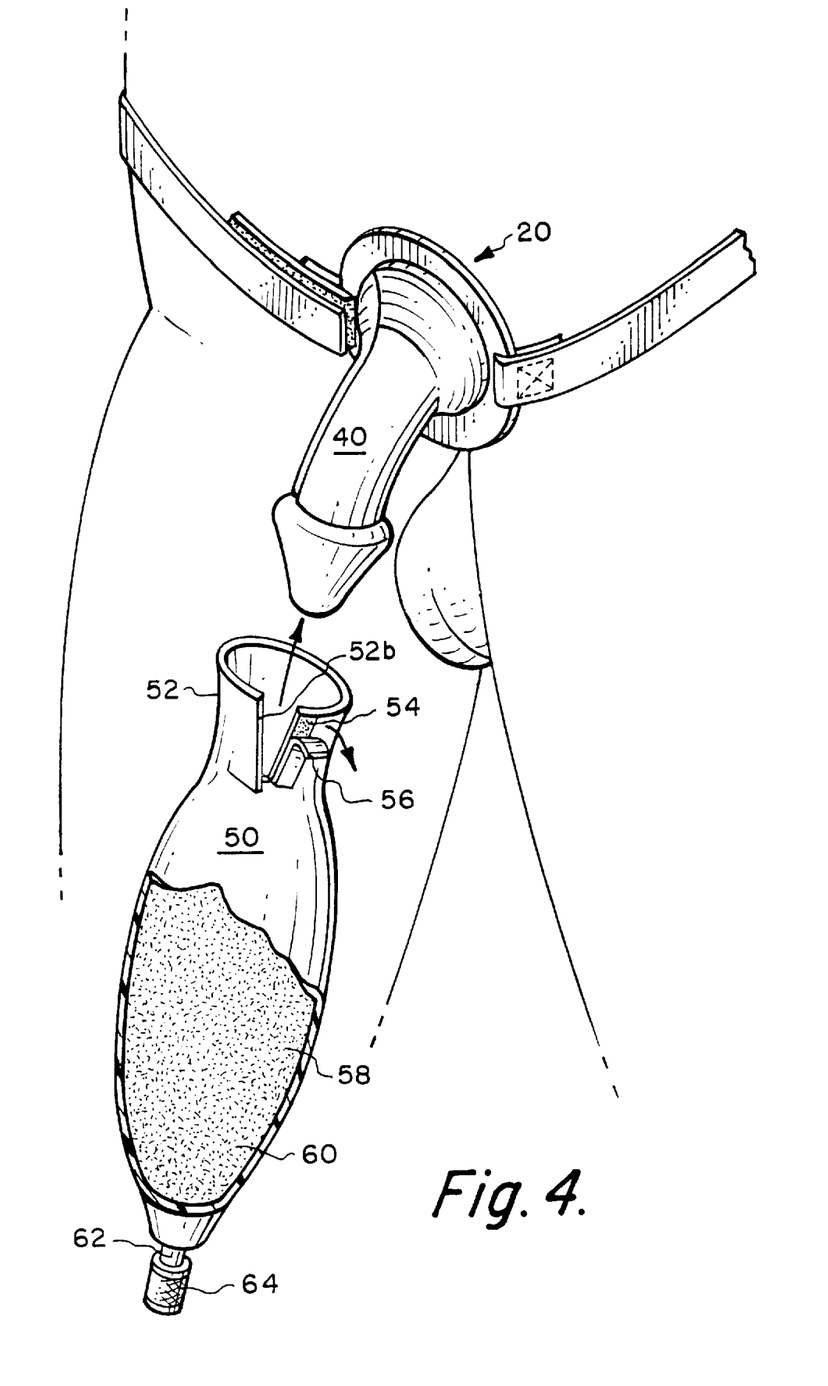
FIG. 4 is a perspective view of a primary fluid chamber positioned to attachment to the attached sheath of FIG. 3.

Referring now to FIG. 4, the penis 10 is depicted wrapped in the sheath 40, which is securely attached to the retention assembly 20. The sheath 40 now forms a stable, fluid tight surface for the mounting of the primary chamber 50, which receives urine expelled by the penis. As shown, the head of the penis is preferably left exposed, but the shaft is wrapped with the sheath, protecting the skin of the shaft from contact with urine. The primary chamber 50 is shown to comprise an attachment band 52, which can comprise a cylindrical inner diameter surface for engaging the sheath 40 deployed about the penis. The illustrative embodiment shows a split band 52, which can be opened to receive the penis 10 therein before securing the band around the sheath-enveloped penis shaft. Of course, other arrangements such as elastic is possible. The illustrative embodiment was designed for one-handed application. An attachment region 54 is provided, which may be an adhesive strip provided with a removable backing 56. Of course other attachment means are usable, such as adhesives, hook and loop fasteners, and the like, or the sheath wrap can be treated over a portion of the surface to form a secure bond to a mating surface. After the attachment band 52 has surrounded the ensheathed penis, the attachment portion 54 is activated and the sheath secured. In the illustrative embodiment, activation of the attachment portion 54 would comprise removing the adhesive backing 56 and pressing the opposite longitudinal region 52b to the exposed adhesive 54. The inside surface of the band 52 and the outside surface of the sheath 40 provide a good anti-slip, high-friction contact, which stably maintains the primary chamber 50 on the penis 10.

The primary chamber 50 forms an interior volume 58, which received urine from the penis. The interior volume may be initially empty, or may contain a gelling chemical known in the art which combines bioactive polymers and enzymes, which upon contact with the urine will gel it into a colloid or semisolid. The bottom portion of the primary chamber 50 can be provided with an emptying neck or tube 62, with a cap 64. Of course, the cap can be replaced with a cock or valve, or may be linked to a secondary chamber such as a bedside bag or reservoir, leg bag, or the like. When connected to a secondary chamber, a check valve and other connecting conduit hardware may be employed as well known in the art.

Figures 5, 6:
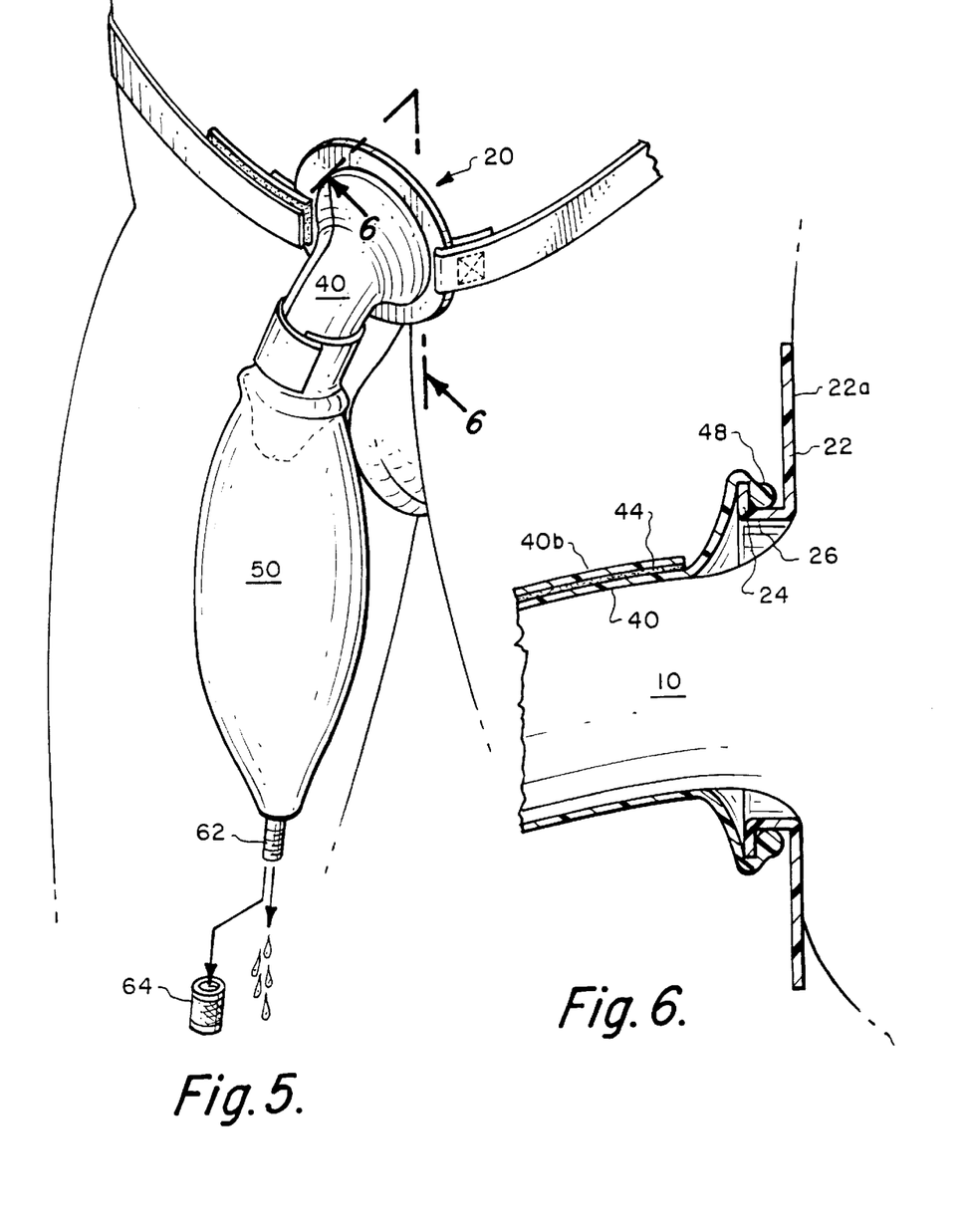
FIG. 5 is a perspective view of the primary fluid chamber of FIG. 4 attached to the sheath.
FIG. 6 is a cross sectional view of the retention ring and sheath taken along section line 6—6 of FIG. 5.

Referring to FIG. 5, the primary chamber 50 of FIG. 4 is shown fully mounted to the sheath wrap 40, surrounding the penis and attached to the retaining assembly 20. The urethra of the penis is therefore in fluid communication directly with the inner volume of the primary chamber. The cap 64, as shown, can be removed from the neck 62 to drain liquid from the interior of the primary chamber 50. The cap 64 is shown to be threadedly attached to the neck 62, but other attachment formats known in the art can be employed.

FIG. 6 is a cross section view taken along line 6—6 of FIG. 5. The attachment of the sheath wrap 40 to the retention assembly is shown in greater detail, revealing the illustrative embodiment. The retention body 22 is shown with a substantially flat side 22a positioned against the body, with the penis 10 extending through the central hole. The attachment flange 24 is shown to provide a groove 26, which receives therein the retention portion 48 of the sheath 40, which in the illustrative embodiment is a thickened bead portion. The sheath 40 is shown disposed about the penis 10, with the longitudinal edge 40b overlying a sheath wrap portion. The assembly is thus stably disposed about the penis.

Figure 7:
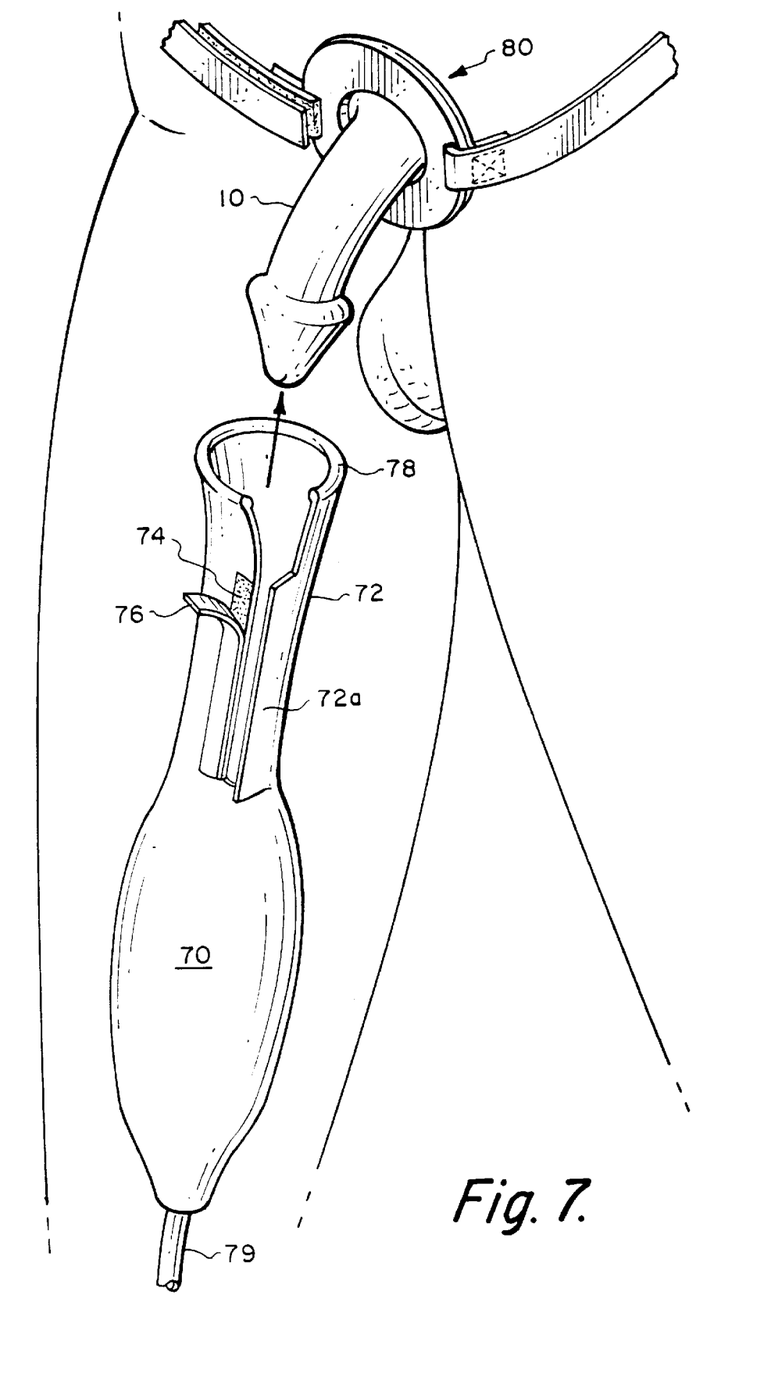
FIG. 7 is a perspective view of an integrated sheath and primary fluid chamber positioned for attachment to a patient.
Figures 8, 9:
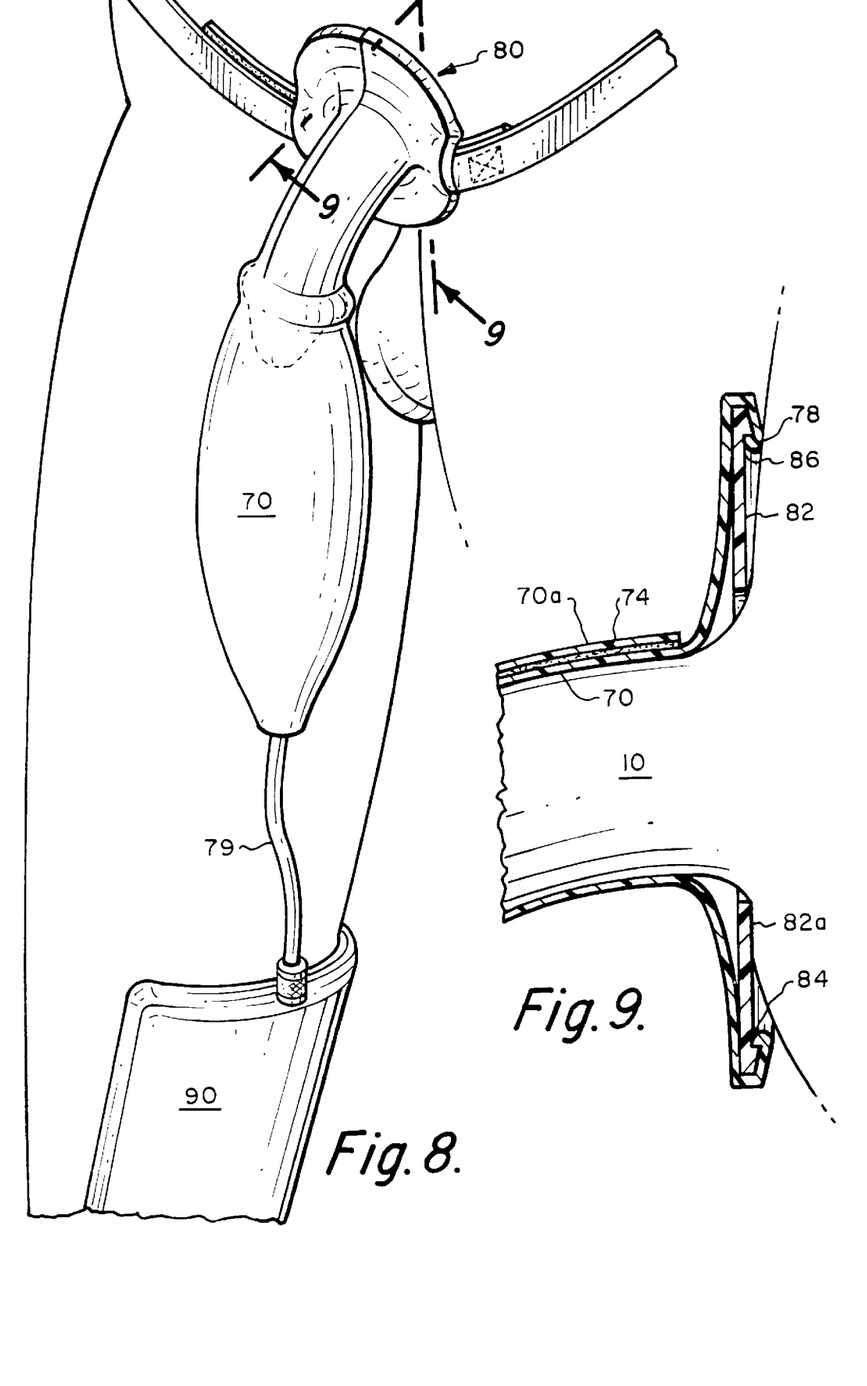
FIG. 8 is a perspective view of the integrated sheath and primary fluid chamber of FIG. 8 mounted on a patient and connected to a secondary fluid chamber.
FIG. 9 is a cross sectional view of the retention ring and sheath taken along section line 9—9 of FIG. 8.

FIG. 7 depicts an alternative embodiment 70 of the present invention where the primary chamber and the sheath wrap are integrated into a single piece. As above, the sheath portion is proximal and the primary chamber distal to the user. A sheath band 72 is provided to surround the penis 10 as above, where a longitudinal region 72a is positionable over a attachment region 74, which in the illustrative embodiment is an adhesive strip with a removable backing 76. A sheath retention portion 78 is disposed circumferentially about the sheath portion, and is receivable in a retention assembly 80, described below. A drain tube 79 can be formed in the bottom of the primary chamber. FIG. 8 depicts the alternative embodiment 70 of FIG. 7 mounted onto the penis, with tube 79 descending to a secondary chamber 90 in the form of a leg bag.

FIG. 9 is a cross section view taken along line 9—9 of FIG. 8. The attachment of the sheath wrap 70 to the retention assembly is shown in greater detail, revealing the alternative illustrative embodiment. The retention body 82 is shown with a substantially flat side 82a positioned against the body, with the penis 10 extending through the central hole. The attachment flange 84 is shown to provide a lip 86 that receives the retention portion 78 of the sheath 70, which in the illustrative embodiment is a thickened bead portion. The sheath 70 is shown disposed about the penis 10, with the longitudinal region 70a overlying a sheath wrap portion. The assembly is thus stably disposed about the penis. This embodiment of the retention body 82 dispenses with the flange of the earlier embodiment, and instead requires that the retention portion 78 of the sheath be applied about the outer circumference of the retention body 82 proper.

Of course, the retention assembly of FIG. 9 is not constrained for use with the integrated sheath and chamber 70 of FIGS. 7–8. The sheath/chamber combinations of this application may be used, when properly configured, in any combination with the retention assemblies herein disclosed.

Figure 10:
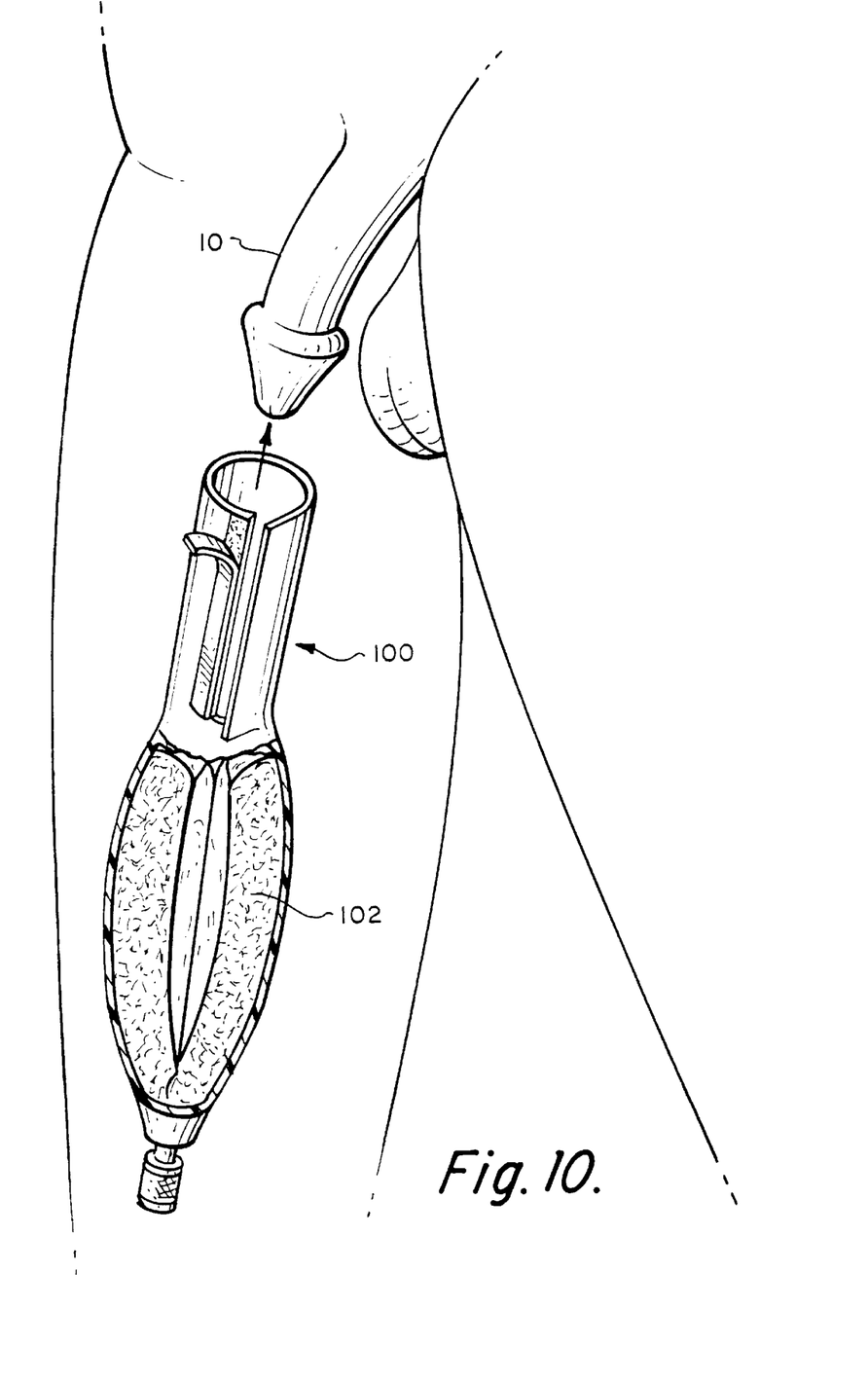
FIG. 10 is a perspective view of another embodiment of an integrated sheath and primary fluid chamber positioned for attachment to a patient.
Figure 11:
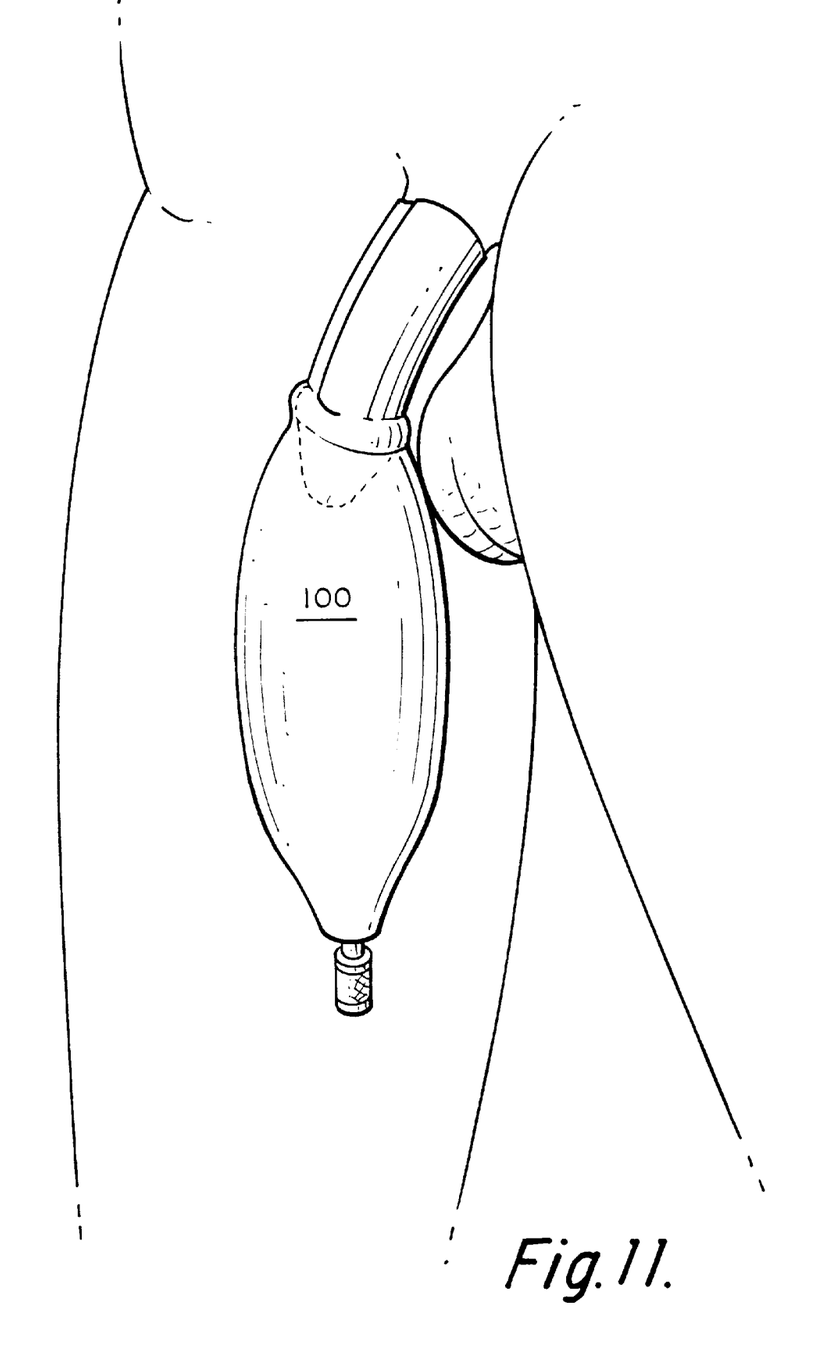
FIG. 11 is a perspective view of the integrated sheath and primary fluid chamber of FIG. 10 mounted on a patient.

FIG. 10 depicts a third alternative embodiment of the present invention which does not require the use of a retention assembly. In this embodiment the combination sheath wrap and chamber 100 is configured substantially the same as the embodiment of FIG. 7, except that there is no retention portion on the sheath at the proximal end thereof. This embodiment is simply wrapped about the penis 10. Additionally, the interior of the chamber may be lined with an absorbent material 102. FIG. 11 depicts the third alternative embodiment being worn by a user.

In applying the invention as hereinabove described, each embodiment is attached to a penis by wrapping the penis in the sheath portion of the device in a circumferential fashion about the surface of the penile shaft. This is in contrast to a condom, which is applied by unrolling material longitudinally from the tip to the base of the penile shaft.

Other devices may also be used in combination with the invention herein described. For example, moisture monitors may be used with the present invention to train against bedwetting and other types of incontinence. In use, a sensor port could be provided in the sheath or primary chamber, or in the drain tube at the distal end of the primary chamber.

Although the invention has been shown and described with respect to exemplary embodiments thereof, various other changes, additions and omissions in the form and detail thereof may be made therein without departing from the spirit and scope of the invention. In addition to the exemplary changes suggested hereinabove, it should also be noted that the various features for managing the urine directed into the interior of the primary chambers hereinabove discussed, viz., absorbent, gelling chemical, tubes, valves, caps, and the like, may be used in any combination with any of the devices herein described, and should not be construed as limited to the specific embodiments which provide context for their exhibition herein.

What is claimed is:

1. An apparatus for forming a fluid tight wrap around a penis of a user comprising:

a substantially fluid impermeable sheath formed of sheet material and having a proximal end and a distal end, a first surface and an opposite, second surface, wherein, in use, the first surface is wrapped about the penis of a user to form an inner surface contacting the skin of the penis, and the opposite, second surface forms an outer surface;

the sheath having a first side and a second side, the first side having an attachment portion on the outer surface, wherein, in use, the first side extends longitudinally down the penile shaft;

the sheath member being sized to circumferentially envelop a penis of a user such that the inner surface of the second side overlaps the attachment portion; and the attachment portion securing the second side to the first side such that the first and second sides overlyingly coextend substantially longitudinally down the penile shaft from the proximal end of the sheath to the distal end of the sheath.

2. A urinary incontinence device comprising the apparatus of claim 1.

3. The urinary incontinence device of claim 2 further comprising a retention body for surrounding the shaft of a penis of a user at a proximal end thereof, the retention body being secured to the body of a user and having a hole for receiving the penile shaft of a user to distally extend the same, the retention body further comprising a retention structure for securing the proximal end of the sheath to the retention body.

4. The urinary incontinence device of claim 3, wherein the sheath member further comprises a retention portion at the proximal end thereof for cooperatively engaging the retention structure of the retention body.

5. The urinary incontinence device of claim 4, wherein the retention portion of the sheath comprises a thickened portion.

6. The urinary incontinence device of claim 5, wherein the retention structure comprises a flange having a groove.

7. The urinary incontinence device of claim 6, wherein the flange is positioned on a front, distal surface of the retention body.

8. The urinary incontinence device of claim 5, wherein the retention structure comprises a lip.

9. The urinary incontinence device of claim 8, wherein the lip is positioned on a back, proximal surface of the retention body.

10. The urinary incontinence device of claim 2, further comprising a primary chamber attached to the sheath and having an interior volume, the interior volume being in fluid communication with the urethra to receive fluid emitted by a penis of a user.

11. The urinary incontinence device of claim 10, wherein the primary chamber further comprises an attachment band, the attachment band connectable to the outer surface of the sheath when attached to a penis of a user, wherein, in use, the interior volume of the primary chamber.

12. The urinary incontinence device of claim 10, wherein the primary chamber is integral with the sheath member at the distal end thereof.

13. The urinary incontinence device of claim 3, wherein the interior volume further comprises a chemical to treat fluid emitted by a user.

14. The urinary incontinence device of claim 10, wherein the interior volume further comprises an absorbent material.

15. A method for applying a sheath to a penis of a user comprising the steps of:

providing a retention body having a hole therein to a user, the hole for receiving a penis of a user;

providing a sheath formed of sheet material and having a proximal end and a distal end, an inner surface and an outer surface, a first side and a second side, the first side having an attachment portion on the outer surface;

enveloping a penis by wrapping the sheath in a circumferential fashion around a penis of a user such that the inner surface of the sheath contacts the skin of a penis of a user and the inner surface of the second side overlaps the attachment portion; and securing the second side to the first side such that the first and second sides overlyingly coextend substantially longitudinally down the penile shaft from the proximal end of the sheath to the distal end of the sheath;

securing the proximal side of the sheath to the retention body.

16. The method of claim 15, further comprising the step of providing a primary chamber having an interior volume, the interior volume being in fluid communication with a urethra of a user.

17. The method of claim 16, further comprising the step of providing a primary chamber having an interior volume, the interior volume being in fluid communication with a urethra of a user.

18. The method of claim 15, wherein the step of providing a sheath further comprises the step of adjusting the sheath for length.

19. A method for applying a sheath to a penis of a user comprising the steps of:

providing a sheath formed of sheet material and having a proximal end and a distal end, a first surface and an opposite, second surface, wherein, in use, the first surface is wrapped about the penis of a user to form an inner surface contacting the skin of the penis, and the opposite, second surface forms an outer surface, a first side and a second side, the first side having an attachment portion on the outer surface;

enveloping a penis by wrapping the sheath in a circumferential fashion around a penis of a user such that the inner surface of the sheath contacts the skin of a penis of a user and the inner surface of the second side overlaps the attachment portion; and securing the second side to the first side such that the first and second sides overlyingly coextend substantially longitudinally down the penile shaft from the proximal end of the sheath to the distal end of the sheath.

20. The method of claim 19, wherein the step of providing a sheath further comprises the step of adjusting the sheath for length.

* * * * *